United States Patent [19]

Polisson et al.

[11] Patent Number: 5,200,337
[45] Date of Patent: Apr. 6, 1993

[54] NOVEL TYPE II RESTRICTION ENDONUCLEASE, APO I, OBTAINABLE FROM ARTHROBACTER PROTOPHORMIAE AND A PROCESS FOR PRODUCING THE SAME

[75] Inventors: Carol Polisson, Arlington; Derek Robinson, Boxford; Keith Lunnen, Newbury, all of Mass.

[73] Assignee: New England Biolabs, Inc., Beverly, Mass.

[21] Appl. No.: 782,515

[22] Filed: Oct. 25, 1991

[51] Int. Cl.⁵ .............................................. C12N 9/22
[52] U.S. Cl. .................................. 435/199; 435/193; 435/320.1; 435/252.33; 536/23.2
[58] Field of Search .............. 435/199, 193, 320.1, 435/252.33; 536/27

[56] References Cited

U.S. PATENT DOCUMENTS

| | | | |
|---|---|---|---|
| 4,983,522 | 1/1991 | Barsomian et al. | 435/172.3 |
| 4,983,542 | 1/1991 | VanCott et al. | 435/172.3 |
| 4,987,074 | 1/1991 | Lunnen et al. | 435/172.3 |
| 4,988,620 | 1/1991 | VanCott et al. | 435/199 |
| 4,996,151 | 2/1991 | Brooks et al. | 435/172.3 |
| 4,999,293 | 3/1991 | Barsomian et al. | 435/172.3 |
| 4,999,294 | 3/1991 | Looney et al. | 435/172.3 |
| 5,002,882 | 3/1991 | Lunnen et al. | 435/172.3 |
| 5,004,691 | 4/1991 | Chen et al. | 435/172.3 |
| 5,015,581 | 5/1991 | Benner, II et al. | 435/172.3 |
| 5,030,569 | 7/1991 | Lunnen et al. | 435/172.3 |
| 5,053,330 | 10/1991 | Lunnen et al | 435/172.3 |
| 5,075,232 | 12/1991 | Morgan | 435/199 |

OTHER PUBLICATIONS

Kessler, C et al. (1990) Gene 92, 1-248.
Lunnen, K. D. et al. (1988) Gene 74, 25-32.
Endow, et al. J. Mol. Biol. 112:521 (1977).
Waalwijk, et al. Nucleic. Acids, Res. 5:3231 (1978).
Gingeras, et al. Proc. Matl. Acad. Sci. USA 80:402 (1983).
Sanger, F. et al. PHAS 74:5463-5467 (1977).
Brown, N. et al. J. Mol. Biol. 140:43-148 (1980).
Birnboin & Doly, Nuculeic Acids Res. 7:1513 (1979).

*Primary Examiner*—Charles L. Patterson, Jr.
*Attorney, Agent, or Firm*—Gregory D. Williams; David G. Conlin

[57] ABSTRACT

The present invention provides a novel type II restriction endonuclease obtainable from *Arthrobacter protophormiae*. The endonuclease known as Apo I, recognizes the following nucleotide sequence and has a cleavage point indicated by the arrows:

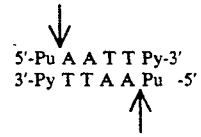

5'-Pu A A T T Py-3'
3'-Py T T A A Pu -5'

Also described is a process for obtaining Apo I from *Arthrobacter protophormiae*.

12 Claims, 1 Drawing Sheet

RESTRICTION MAP OF A 4.8kb BglII FRAGMENT ENCODING THE ApoI METHYLASE AND RESTRICTION GENES CLONED FROM *ARTHROBACTER PROTOPHORMIAE*

NOVEL TYPE II RESTRICTION ENDONUCLEASE, APO I, OBTAINABLE FROM ARTHROBACTER PROTOPHORMIAE AND A PROCESS FOR PRODUCING THE SAME

BACKGROUND OF THE INVENTION

The present invention relates to a new Type II restriction endonuclease, Apo I, obtainable from *Arthrobacter protophormiae* and for processes for producing the same.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. The majority of restriction endonucleases recognize sequences of 4 to 6 nucleotides in length, although recently a small number of restriction endonucleases which recognize 7 or 8 uniquely specified nucleotides have been isolated. Most recognition sequences contain a dyad axis of symmetry and in most cases all the nucleotides are uniquely specified. However, some restriction endonucleases have degenerate or relaxed specificities in that they recognize multiple bases at one or more positions in their recognition sequence, and some restriction endonucleases recognize asymmetric sequences. Hae III, which recognizes the sequence 5' GGCC 3', is an example of a restriction endonuclease having a symmetrical, non-degenerate recognition sequence, while Hae II, which recognizes 5' (Pu)GCGC(Py) 3' typifies restriction endonucleases having a degenerate or relaxed recognition sequence. Endonucleases with symmetrical recognition sequences generally cleave symmetrically within or adjacent to the recognition site, while those that recognize assymmetric sequences tend to cleave at a distance of from 1 to 18 nucleotides away from the recognition site. Over one hundred twenty-five unique restriction endonucleases have been identified among several thousands of bacterial species that have been examined to date.

Bacteria usually possess only a small number of restriction endonucleases per species. The endonucleases are named according to the bacteria from which they are derived. Thus, the species *Haemophilus aegyptius*, for example synthesizes 3 different restriction endonucleases, named HaeI, HaeII and HaeIII. These enzymes recognize and cleave the sequences (AT)GGCC(AT), PuGCGCPy and GGCC respectively. *Escherichia coli* RY13, on the other hand, synthesizes only one enzyme, EcoRI, which recognizes the sequence GAATTC.

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by binding to infecting DNA molecule and cleaving them in each place that the recognition sequence occurs. The disintegration that results inactivates many of the infecting genes and renders the DNA susceptible to further degradation by exonucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the restriction endonuclease. The DNA of a bacterial cell is always fully modified, by virtue of the activity of its modification methylase and it is therefore completely insensitive to the presence of the endogenous restriction endonuclease. It is only unmodified, and therefore identifiably foreign, DNA that is sensitive to restriction endonuclease recognition and attack.

More than 1000 restriction endonucleases have been isolated from bacterial strains. Of these, more than 125 recognize unique sequences, while the rest share common recognition specificities. Restriction endonucleases which recognize the same nucleotide sequence are termed "isoschizomers." Although the recognition sequences of isoschizomers are the same, they may vary with respect to site of cleavage (e.g., XmaI v. SmaI, Endow, et al., J. Mol. Biol. 112:521 (1977); Waalwijk, et al., Nucleic Acids Res. 5:3231 (1978)) and in cleavage rate at various sites (XhoI v. PaeR7I, Gingeras, et al., Proc. Natl. Acad. Sci. U.S.A. 80:402 (1983)).

There is a continuing need for novel type II restriction endonucleases Although type II restriction endonucleases which recognize a number of specific nucleotide sequences are currently available, new restriction endonucleases which recognize novel sequences provide greater opportunities and ability for genetic manipulation. Each new unique endonuclease enables scientists to precisely cleave DNA in new places, with all the opportunities this offers.

SUMMARY OF THE INVENTION

In accordance with the present invention, there is provided a novel restriction endonuclease obtainable from *Arthrobacter protophormiae* NEB#723, hereinafter referred to as "ApoI", which endonuclease:

(1) recognizes the nucleotide sequence PuAATTPy in a double-stranded DNA molecule as shown below,

(wherein Pu represents guanine or adenine, Py represents cytosine or thymine, A represents adenine, and T represents thymine);

(2) cleaves said sequence in the phosphodiester bonds between the first and second 5' base pairs to create a 4-base 5' extension as indicated with the arrows; and (3) Apo I has the following number of recognition sites on these DNAs: pUC19 (1), pBR322 (1), phiX174 (7), M13mp18 (11), T7 (13), Lambda (58), and Adeno2 (29).

The present invention further relates to processes for the production of the novel restriction endonuclease Apo I. One process comprises culturing *Arthrobacter protophormiae* under conditions suitable for expressing Apo I, collecting the cultured cells, obtaining a cell-free extract therefrom and separating and collecting the restriction endonuclease Apo I from the cell-free extract. The other process comprises cloning Apo I R-M system by forming a library containing the DNA from *Arthrobacter protophormiae*, isolating those clones which contain DNA coding for the Apo I modification methylase and screening these to identify those that also contain the Apo I restriction endonuclease gene. Recombinant Apo I can be obtained by culturing the host cell containing the DNA encoding the Apo I endonuclease under conditions suitable for expressing Apo I, collecting the cultured cells, obtaining a cell-free extract therefrom and separating and collecting the restriction endonuclease Apo I from the cell-free extract.

DETAILED DESCRIPTION OF THE INVENTION

Figure 1:
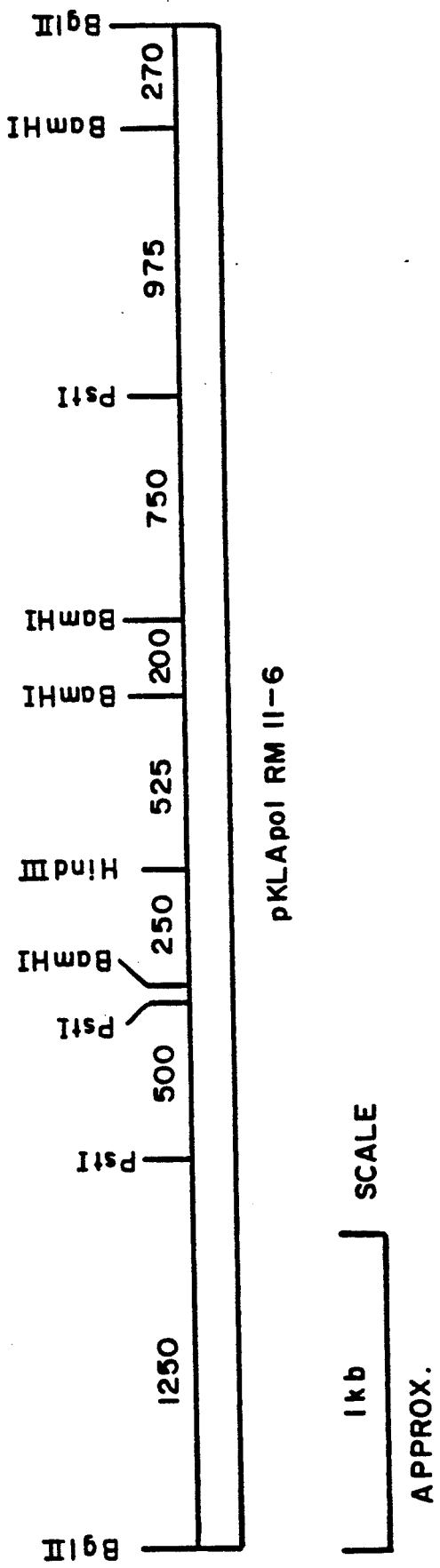
FIG. 1 is a restriction map of the 4.8 kb Bgl II fragment from Arthrobacter encoding the Apo I restriction endonuclease and modification methylase.

The recognition sequence of the endonuclease of the present invention was determined by complete digestion of phiX174 DNA with Apo I. The size of the resulting fragments was determined by agarose gel electrophoresis. The sizes of the experimentally observed fragments were 2680, 1325, 550, 320, 225 and 70 base pairs. The computer calculated (Devereaux J., et al., (1984) NAR 12:387-395) number and sizes of the fragments that would be generated by cleavage at the 5' PuAATTPy 3': 2690, 1290, 554, 326, 239, 185 and 102 base pairs, correlate with the observed fragments. To further test the recognition sequence, 6 other DNA molecules were digested with Apo I and electrophoresed using a 1.0% agarose gel. These DNA molecules were pUC19, pBR322, M13mp18, T7, Lambda, and Adeno-2 and contain the following number of PuAATTPy sequences respectively; 1, 1, 11, 13, 58, 29. The experimentally observed numbers and sizes of the resulting DNA fragments matched the computer predicted fragments that would be generated by cleavage at 5' PuAATTPy 3'. From this data, we conclude that Apo I recognizes the sequence 5' PuAATTPy 3'.

The point of cleavage within the Apo I recognition sequence was determined through dideoxy sequencing analysis of the terminal base sequence obtained from Apo I cleavage (Sanger, F. et al., (1977) PNAS 74:5463-5467, Brown, N. L., et al., (1980) J. Mol. Biol. 140:43-148). Using M13mp18 DNA as template with an appropriate primer, the four standard dideoxy DNA sequencing reactions were performed and a fifth reaction containing no dideoxy terminations was extended through the Apo I site. The fifth reaction was terminated by heat treatment to inactivate the Klenow DNA polymerase. Apo I was added to the fifth reaction. The cleaved product resulted in a single band which comigrates with the 5' Pu in the sequence 5' GAATTC 3'. The addition of Klenow subsequent to Apo I digestion, results in a band which is four nucleotides longer, comigrating with the 3'-most T residue. These results indicate that Apo I cleaves after the first purine residue of the recognition sequence in the 5' to 3' direction on both strands producing a symmetric four base 5' overhang, as indicated by the arrows:

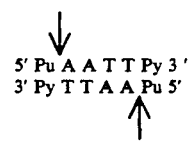

The enzyme of the present invention has the following additional properties:

(a) NaCl Concentration: The optimal salt concentration was at 50 mM NaCl, the relative activity being 25% for 0 mM NaCl and 50% for 100 mM NaCl.

(b) Temperature: Activity was higher at 50° C. than at 37° C. or 60° C.

(c) Stability: 0.13 unit (as defined below) of Apo I was required to completely cleave 1 mg of lambda phage in 16 hours at 50° C. Forty units of Apo I could not be completely inactivated by pre-treatment at 65° C. for 20 minutes.

In accordance with the current invention, ApoI is obtained by culturing *Arthrobacter protophormiae* strain NEB#723 and recovering the endonuclease from the cells. A sample of *Arthrobacter protophormiae* NEB#723 has been deposited at the American Type Culture Collection on Aug. 30, 1991 and bears the accession number ATCC 55228.

For recovering the enzyme of the present invention *A. protophormiae* may be grown using any suitable technique. For example, *A. protophormiae* may be grown in a media comprised of 10 g/L tryptone, 5 g/L yeast extract, 10 g/L NaCl, 1 g/L dextrose, 1 g/L $MgCl_2.6H_2O$ (pH 7.2), which is incubated at 30° C. with agitation and aeration. Cells in the late logarithmic stage of growth are collected by centrifugation and either disrupted immediately or stored frozen at −70° C.

The Apo I enzyme is preferably isolated from A. protophormiae cells as follows: Cell paste is suspended in a buffer solution and treated by sonication, high pressure dispersion or enzymatic digestion to allow extraction of the endonuclease by the buffer solution. Intact cells and cellular debris is then removed by centrifugation to produce a cell-free extract containing Apo I. The Apo I endonuclease is then purified from the cell-free extract by ion-exchange chromatography, affinity chromatography, molecular sieve chromotography, or a combination of these methods to produce the endonuclease of the present invention.

The enzyme of this invention may also be produced by recombinant DNA techniques, as the gene encoding this enzyme has been cloned from *Arthrobacter Protophormiae* genomic DNA. The complete coding sequence for the Apo I restriction endonuclease and methylase gene can be derived from the plasmid pKLApoIRMII-6. This plasmid was deposited with the American Type Culture Collection (ATCC) on Oct. 7, 1991 and has Accession No. ATCC 75119.

The present invention relates to clones of the Apo I restriction and modification genes, as well to the restriction endonuclease Apo I produced from such clones. The Apo I genes are cloned by a method which takes advantage of the fact that certain clones which are selected on the basis of containing and expressing the Apo I modification or methylase gene also contain the Apo I restriction gene. The DNA of such clones is resistant to digestion, in vitro, by the Apo I restriction endonuclease. This resistance to digestion affords a means for selectively isolating clones encoding the Apo I methylase and restriction endonuclease.

The following examples are given to illustrate embodiments of the present invention as it is presently preferred to be practiced. It will be understood that the examples are illustrative, and that the invention is not to be considered as restricted thereto except as indicated in the appended claims.

EXAMPLE I

Purification of Apo I from *Arthrobacter protophormiae*

*Arthrobacter protochormiae* strain NEB #723 was grown in a media consisting of 10 g/l tryptone, 5 g/l yeast extract, 5 g/l NaCl (adjusted to pH 7.2). The cells were incubated at 30° C. until late logarithmic stage with aeration and agitation. The cells were harvested by centrifugation and the resulting cell paste stored frozen at −70° C.

262 grams of the cell paste obtained above were thawed and suspended in three volumes buffer A (20 mM Tris-HCl, 0.1 mM EDTA, 6 mM 2-mercaptoethanol, 5% glycerol, pH 8.0) adjusted to 100 mM NaCl. The cell suspension was passed 6 times through a Gaulin press at 12,000 PSI. Approximately 31 mg of protein/gram of cells was released. The lysate was centrifuged at 4° C. for 40 minutes. The supernatant volume was 900 mls at pH 7.3. The debris weight was 160 g. The supernatant contained 7,200,000 units of Apo I.

The supernatant solution was loaded onto a 353 ml DEAE-Sepharose column (Pharmacia) equilibrated in buffer A adjusted to 100 mM NaCl. The flow through was batch collected. The column was washed with 400 ml of buffer A adjusted to 100 mM NaCl. The flow through and wash were combined. The combined DEAE flow through and wash pool contained 2,600,000 units of Apo I in 1300 ml. The DEAE column was eluted with a 2 liter gradient of 100 mM to 700 mM NaCl in Buffer A. Additional Apo I activity eluted from 34–41% of the gradient volume. Two hundred mls containing 1,600,000 units of Apo I activity were pooled and dialysed against buffer A adjusted to 100 mM NaCl.

The DEAE flow through and wash pool was loaded onto a 59 ml Heparin-Sepharose column equilibrated in buffer A adjusted to 100 mM NaCl. The column was washed with 300 ml of buffer A adjusted to 100 mM NaCl. The enzyme was eluted with a 600 ml gradient of 100 mM to 1M NaCl in buffer A. Fractions were tested for Apo I and exonuclease activity. The Apo I activity eluted from 56–68% of the gradient volume. The majority of exonuclease activity eluted from 0–58% of the gradient volume. The DEAE column bound pool was loaded, washed and eluted from the heparin sepharose column as above. The fractions containing Apo I activity from both heparin sepharose column purifications were pooled and dialysed against buffer B (20 mM KPO4, 6 mM 2-mercaptoethanol, 0.1 mM EDTA, 5% glycerol, pH 6.7 ) adjusted to 100 mM NaCl.

The 200 ml dialysate containing 200 mg of protein was applied to a 17 ml Whatman phosphocellulose column, equilibrated in buffer B adjusted to 100 mM NaCl. The column was washed with 100 ml of buffer B adjusted to 100 mM NaCl. The enzyme was eluted with a 200 ml gradient of buffer B from 100 mM to 1M NaCl. The Apo I activity eluted from 38% to 53% of the gradient volume. The phosphocellulose pool containing 3,200,000 units of Apo I in 50 ml was dialysed against buffer C (20 mM KPO4, 6 mM 2-mercaptoethanol, 0.1 mM EDTA, 5% glycerol, pH 6.3 ) adjusted to 50 mM NaCl. The majority of the exonuclease activity eluted at approximately 35% of the gradient volume.

The dialysate containing 100 mg of protein was divided into three equal aliquots and three seperate 7.5 MMID TSK-GEL Heparin-5 PW (TosoHaas) columns were run. These were equilibrated in buffer C adjusted to 50 mM NaCl. The protein solution was eluted with a 70 ml gradient of 50 mM to 0.7M NaCl in buffer C. The Apo I activity eluted at 0.6M NaCl. The majority of the exonuclease activity eluted at 0.43M NaCl. The combined 4 ml pool of Apo I from the three column runs contained 1,600,000 units. This pool was diluted to 50 mM NaCl with buffer B.

The diluted Heparin-5PW was applied to a WCX 7 μm HPLC column (Custom LC, Inc.) equilibrated in buffer B adjusted to 50 mM NaCl. The protein solution was eluted with a 50 ml gradient of 50 mM to 0.6M NaCl in buffer B. The Apo I activity eluted at 0.42M NaCl. The Apo I activity was pooled and found to be substantially free of contaminating DNA binding protein, exonuclease and endonuclease. Bovine serum albumin was added as a stabilizer to give a final concentration of 200 μg/ml and the Apo I was dialysed against storage buffer (50 mM NaCl, 20 mM Tris-HCl, 0.1 mM EDTA, 1.0 mM dithiothreitol, 50% glycerol, pH 7.5). This final Apo I pool was substantially pure and contained 1,500,000 units, a 20% recovery.

Activity Determination

Apo I activity: A 1 μl sample of the fraction to be assayed was added to 25 μl of the substrate reaction buffer solution (50 mM NaCl, 10 mM Tris-HCl, 10 mM MgCl$_2$ 1 mM dithiothreitol, pH 7.9 containing 0.5 μg lambda phage DNA), supplemented with 100 μg/ml bovine serum albumin. The enzymatic reaction was incubated at 50° C. for the time indicated, 5–30 minutes. The reaction was terminated by adding 7.0 μl of a Stop solution (50% glycerol, 50 mM EDTA pH 8.0, and 0.02% Bromophenol Blue). The reaction mixture was applied to a 1.0% agarose gel and electrophoresed. The bands obtained were identified in comparison with DNA length standards.

Exonuclease activity: A 5 μl sample of the protein solution was added to 50 μl of (50 mM NaCl, 10 mM Tris-HCl, 10 mM MgCl$_2$,1 mM dithiothreitol, pH 7.9 containing 25 μg/ml $^3$H DNA). Supplemented with 100 μg/ml bovine serum albumin. The enzymatic reaction was incubated at 50° C. for the time indicated, 1–4 hours.

Unit Definition: One unit of Apo I completely cleaves 1 μg of Lambda phage DNA in one hour at 50° C.

Optimum Buffer Conditions: For optimum Apo I activity the following buffer was used: 50 mM NaCl, 10 mM Tris-HCl, 10 mM MgCl2, 1 mM dithiothreitol, pH

EXAMPLE II

Cloning of Apo I Restriction Endonuclease and Methylase Genes

1. DNA Purification

To prepare the DNA of *Arthrobacter protophormiae*, 5 gm of cell paste was resuspended in 10 ml of 25% sucrose, 50 mM Tris-HCl pH 8.0, 5 ml of 0.25M EDTA pH 8.0, and 3 ml of 10 mg/ml lysozyme in 0.25 M Tris pH 8.0 were added. The suspension was kept on ice for 1 hour, then 12 ml of 1% Triton X-100, 50 mM Tris pH 8.0, 67 mM EDTA was added to the solution and placed at 37° C. for 2 hours. Cell lysis was incomplete so the DNA solution was placed at 4° C. for 64 hours. SDS was added to 0.1% and the solution was extracted with 30 ml of phenol, (previously equilibrated with 0.5 M Tris pH 8.0), and 30 ml of chloroform. The emulsion was centrifuged at 15,000 rpm for 10 minutes to remove solid debris. The clarified supernatant was added to dialysis tubing and dialysed against four changes of DNA Buffer (10 mM Tris pH 8.0, 1 mM EDTA pH 8.0). The dialysed solution was then digested with RNase at a final concentration of 100 mg/ml for 1 hour at 37° C. The DNA was then precipitated by the addition of 5M NaCl to a final of 0.4 M, and 0.55 volumes of isopropyl alcohol. The precipitated DNA was spooled onto a glass rod, air-dried, then redissolved in DNA buffer to a final concentration of approximately 100 $\mu$g/ml and stored at 4° C.

2. Partial Digestion

The purified DNA was cleaved with BglII to achieve partial digestion as follows: 0.45 ml of DNA at 50 $\mu$g/ml in 50mM Tris pH 7.9, 10mM MgCl$_2$, 100 mM NaCl and 1 mM DTT was divided into one 100 $\mu$l aliquot and seven, 50 $\mu$l aliquots. To the 100 $\mu$l tube was added 40 units of BglII to achieve 8.0 units of enzyme per ug of DNA. 50 $\mu$l was withdrawn from the first tube and transferred to the second tube to achieve 4 units BglII/$\mu$g, and so on, each succeeding tube receiving half of the previous amount of BglII. The tubes were incubated at 37° C. for one hour, then heat-treated at 72° C. for 10 minutes and 10 $\mu$l from each was analyzed by agarose gel electrophoresis. Tubes exhibiting moderate, but incomplete digestion were pooled separately from those tubes exhibiting complete digestion as the source for cloning.

3. Ligation

The fragmented DNA was ligated to pBR322 as follows: 2.0 $\mu$g of BglII—completely or partially digested *A. protophormiae* DNA (40 $\mu$l) was mixed with 1.0 $\mu$g of BamHI-cleaved and dephosphorylated pBR322 (10 $\mu$l). 10 $\mu$l of 10 X ligation mix (500 mM Tris, pH 7.8, 100 mM MgCl$_2$, 200 mM DTT, 10 mM ATP, 500 mg/ml bovine serum albumin) was added, plus 44 $\mu$l of sterile distilled water to bring the final volume to 100 $\mu$l 3.75 $\mu$l of T4 DNA ligase was added and the mixture was incubated at 17° C. for overnight then sterilized by the addition of 10 $\mu$l of chloroform. Approximately 32 $\mu$l of the ligated DNA from each BglII complete and the partial pool was used to transform *E. coli* strain RR1 as follows: 64 $\mu$l of DNA (32 $\mu$l of BglII complete + 32 $\mu$l of BglII partial ligated pools) was mixed with 0.5 ml of SSC/CaCl$_2$ (50 mM NaCl, 5 mM Na$_3$ Citrate, 67 mM CaCl$_2$) on ice and 1.0 ml of ice-cold competent *E. coli* RR1 (hsd R$^-$M$^-$, ATCC No. 31343) cells were added. After a 6-minute incubation at 43° C., the cells were diluted by the addition of 8 ml of Luria-broth (L-broth) then incubated at 37° C. for 4 hours.

4. Primary Cell Library

The transformed cell culture was briefly centrifuged, the supernatant was discarded and the cells were resuspended in 1.0 ml of L-broth. 200 $\mu$l portions were plated onto Luria-agar (L-agar) plates containing 100 $\mu$g/ml ampicillin. After overnight incubation at 37° C., the plates were each flooded with 2.5 ml of 10 mM Tris, pH 7.5, 10 mM MgCl$_2$ and the transformed colonies were scraped together and pooled to form the primary cell library.

5. Primary Plasmid Library

The primary plasmid library was prepared as follows: 2.5 ml of the primary cell library was inoculated into 500 ml of L-broth containing 100 $\mu$g/ml ampicillin. The culture was shaken overnight at 37° C. then centrifuged at 4000 rpm for 5 minutes. The supernatant was discarded and the cell pellet was resuspended in 10 ml of 25% sucrose, 50 mM Tris, pH 8.0, at room temperature. 5 ml of 0.25M EDTA, pH 8.0, was added, followed by 3 ml of 10 mg/ml lysozyme in 0.25 M Tris, pH 8.0. The solution was left on ice for 1 hour, then 12 ml of lytic mix (1% Triton X-100, 50 mM Tris, pH 8.0, 67 mM EDTA) was forcefully pipetted in, and the cell suspension gently swirled to achieve lysis. After lysis, the mixture was transferred to a 50 ml plastic centrifuge tube and spun at 17000 rpm, 4° C. for 45 minutes. The supernatant was removed with a pipette. 20.0 gm of solid CsCl was weighed into a 50 ml plastic screw-cap tube and 22.0 gm of supernatant was pipetted into the tube and mixed. 1.0 ml of ethidium bromide solution (5 mg/ml ethidium bromide in 10 mM Tris, pH 8.0, 1 mM EDTA, 100 mM NaCl) was added to the mixture. The solution was transferred to two ⅝in.×3 in. polyallomer centrifuge tubes and sealed. These tubes were then spun in a Beckman Ti70 rotor for 42 hours at 44000 rpm, 17° C.. To collect the plasmids, the tops of the tubes were pierced with a scalpel and the lower of the two fluorescent DNA bands was collected by syringe under ultraviolet light. The lower band from both tubes was combined into a screw-top glass tube and the ethidium bromide was removed by extracting four times with an equal volume of water-saturated ice-cold N-Butanol.

The extracted solution was transferred to dialysis tubing and dialyzed for 24 hours against 4 changes of DNA buffer. The dialyzed DNA solution was then transferred to a pre-weighed 50 ml sterile centrifuge tube and its volume was measured. 5M NaCl was added to a final concentration of 0.4M, then 2 volumes of isopropanol were added and mixed. The solution was stored overnight at −20° C. to precipitate the DNA. After precipitation, the solution was spun at 15000 rpm, 4° C. for 15 minutes and the supernatant discarded. The tube was left on the bench to air-dry for 15 minutes, then the DNA pellet was dissolved in 500 $\mu$l of DNA buffer and stored at −20° C. The DNA concentration of plasmids prepared in this way were found to be approximately 30 $\mu$g/ml.

6. Digestion of Plasmid Pool

The BglII primary plasmid pool was digested to destroy non-Apo I methylase clones as follows: 1.0 μg (35 μl) of plasmid DNA was mixed with 50mM Tris pH 7.9, 10 mM MgCl$_2$, 1 mM DTT, 100 mM NaCl, 100 μg/ml BSA in a volume of 45 μl and Apo I was added to 16u/μg DNA. The tube was incubated at 37° C. for 2 hour. The reaction were inactivated by heating to 72° C. for 10 minutes, then placed on ice for 5 minutes. 1 μl (10 units) of CIAP the tube was placed at 37° C. for 1 hour.

7. Transformation

A 12.5 μl sample from the tube was used to transform *E. coli* RR1. The cell/DNA mixtures were plated onto L-agar plates containing 100 μg/ml ampicillin immediately after the heat step, without intermediate dilution and growth. After overnight incubation at 37° C., the plates were examined. Digestion of the plasmid library with Apo I and followed by treatment with CIAP was found to have reduced the number of transformants by a factor of greater than 10$^3$. Fourteen individual colonies were picked from the plate and each colony was inoculated into 10 ml of L-broth containing ampicillin, to prepare a miniculture, and was also streaked onto L-agar plates containing ampicillin to prepare a master stock.

8. Analysis of Surviving Individuals

Approximately 14 of the surviving colonies obtained from section 7 were grown up into 10 ml cultures (section 7) and the plasmids that they carried were prepared by the following miniprep purification procedure, adapted from the method of Birnboin and Doly (Nucleic Acids Res. 7: 1513 (1979)).

Miniprep Procedure

Each culture was centrifuged at 5000 rpm for 5 minutes; the supernatant was discarded and the cell pellet was resuspended in 1.0 ml of 25 mM Tris, 10 mM EDTA, 50 mM glucose, pH 8.0, containing 1 mg/ml lysozyme. After 1 minute at room temperature, 2.0 ml of 0.2M NaOH, 1% SDS was added to each tube and the tubes were shaken to lyse the cells. Once the solutions had cleared, 1.5 ml of 3M sodium acetate, pH 4.8, was added to each and shaken. The precipitates that formed were spun down at 15000 rpm, 4° C. for 10 minutes. Each supernatant was poured into a centrifuge tube containing 3 ml of isopropanol and mixed. After 10 minutes at room temperature, the tubes were spun at 15000 rpm for 10 minutes to pellet the precipitated nucleic acids. The supernatants were discarded and the pellets were air-dried at room temperature for 30 minutes. Once dry, the pellets were resuspended in 850 μl of 10 mM Tris, 1 mM EDTA, pH 8.0. 75 μl of 5M NaCl was added to each and the solutions were transferred to Eppendorf tubes containing 575 μl of ice-cold isopropanol, and again precipitated for 10 minutes at room temperature. The tubes were then spun for 45 seconds in a microfuge, the supernatants were discarded and the pellets were air-dried. The pellets were then dissolved in 500 μl of 10 mM Tris, 1 mM EDTA, pH 8.0, containing 100 μg/ml RNase and incubated for 1 hour at 37° C. to digest the RNA. The DNA was precipitated once more by the addition of 50 μl of 5M NaCl followed by 350 μl of isopropanol. After 1 minute at room temperature, the DNA was spun down by centrifugation for 45 seconds, the supernatants were discarded and the pellets were redissolved in a final solution of 150 μl of 10 mM Tris 1 mM EDTA, pH 8.0. The plasmid minipreps were subsequently analyzed by digestion with Apo I.

9. Methylase Gene Clones

The majority of the plasmids that were analyzed were found to be sensitive to digestion by Apo I and to carry random fragments of *Arthrobacter protophormiae* DNA. These plasmids were spurious survivors, of no further interest, and were discarded. Four of the fourteen were resistant to Apo I digestion. One of these four plasmids from the pBR322 BglII library was not only resistant to Apo I, but carried a BglII fragment of approximately 4.8 Kb (See FIG. 1) and was subsequently shown to carry not only the Apo I modification methylase gene but also restriction endonuclease gene.

10. Restriction Gene Clone

The BglII clone identified above (section 9) as carrying the Apo I modification methylase gene was transferred to *E. coli* strain MM294 (ATCC 33625). The BglII clone was found to carry the Apo I restriction endonuclease gene by in vitro restriction endonuclease assay:

Endonuclease Assays

To assay for endonuclease activity, two solutions were prepared:
(i) 10× restriction endonuclease buffer: 500 mM Tris, pH 7.9, 100 mM MgCl$_2$, 10 mM DTT, 1000 mM NaCl; and (ii) digestion reaction mix: 40 μl phage T7 DNA (250 μg/ml), 45 μl 10× restriction endonuclease buffer, 361 μl distilled water to achieve 25 μg/ml DNA.

The cell extract was prepared as follows: A 100 ml culture of the clone to be tested was grown overnight in L-broth plus 100 μg/ml ampicillin at 37° C. and the cells were pelleted by centrifugation at 4000 rpm for 5 minutes. The supernatant was discarded and the pellet was resuspended in 3 ml of sonication buffer (75 mM KPO$_4$ pH 7.0, 10 mM BME, 0.1 mM EDTA). Once resuspended, 0.3 ml of sonication buffer containing 10 mg/ml lysozyme was added. The suspension was swirled and left on ice for 1 hour. A 1 ml sample was transferred to an Eppendorf tube and sonicated gently for two 20-second bursts to disrupt the cells. The tube was spun for 5 minutes in a microfuge and the supernatant was used as the cell extract. To assay the extract, the digestion reaction mix was dispensed into 4 tubes, 75 μl into the first tube and 50 μl into each of the remaining 3 tubes. 3 μl of the extract was added to the first tube and mixed. 25 μl was removed from the first tube and transferred to the second tube, mixed and so on. The first tube thus received approximately 1.5 μl of extract per μg of DNA, the second tube 0.5 μl/μg, the third tube, 0.15 μl/μg and the fourth tube, 0.05 μl/μg . The tubes, each now containing 50 μl, were incubated at 50° C. for one hour, then a 20 μl sample of each was analyzed by gel electrophoresis. The titre of the extract was found to be greater than 1×10$^3$ units of Apo I restriction endonuclease per gram of wet cell paste.

11. Production of the Apo I endonuclease may be produced from the recombinant plasmid pKLApoIRM 11-6 carrying the Apo I modification gene and endonuclease gene by propagation in a fermenter in a rich medium containing ampicillin. The cells are thereafter harvested by centrifugation and disrupted by sonication to produce a crude cell extract containing Apo I endonuclease activity.

The crude cell extract containing the Apo I endonuclease is purified by standard product purification techniques such as affinity-chromatography, or ion-exchange chromatography.

What is claimed is:

1. A substantially pure Type II restriction endonuclease ApO I obtainable from *Arthrobacter protophormiae* (ATCC#55228) which recognizes and cleaves all permutations of the following base sequence in double-standard deoxyribonucleic acid molecules:

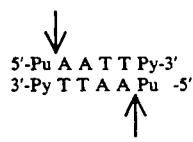

and having a cleavage defined by the arrows.

2. The type II restriction endonuclease of claim 1, cleaving double-stranded deoxyribonucleic acid lambda cI857 in 58, adeno-2 in 29, and pBR322 in 1 position.

3. A method for obtaining the Type II restriction endonuclease of claim 1, comprising cultivating a sample of *Arthrobacter protophormiae* under conditions favoring the production of said endonuclease and separating said endonuclease therefrom.

4. The type II restriction endonuclease of claim 1, wherein the restriction endonuclease is purified from *Arthrobacter protophormiae* (ATCC#55228).

5. The type II restriction endonuclease of claim 1, wherein the restriction endonuclease is purified from a transformed host containing the DNA sequence encoding the restriction endonuclease.

6. Isolated DNA coding for the Apo I restriction endonuclease of claim 1, wherein the isolated DNA is obtainable from the vector pKLApoIRM11-6.

7. A recombinant DNA vector comprising a vector into which a DNA segment coding for the Apo I restriction endonuclease of claim 1 has been inserted.

8. Isolated DNA coding for the Apo I restriction endonuclease and methylase of claim 1, wherein the isolated DNA is obtainable from vector pKLApoIRM11-6.

9. A cloning vector which comprises the isolated DNA of claim 8.

10. The cloning vector of claim 9, wherein the cloning comprises pKLApoIRM11-6.

11. A host cell transformed by the cloning vector of claim 7, 9 or 10.

12. A method of producing an Apo I restriction endonuclease comprising culturing a host cell transformed with the vector of claim 7, 9 or 10 under conditions suitable for expression of said endonuclease.

* * * * *